United States Patent [19]

Lempert et al.

[11] 4,435,322
[45] Mar. 6, 1984

[54] HETEROCYCLIC COMPOUNDS CONTAINING AN ALKOXYCARBONYL AND A SUBSTITUTED METHYL GROUP

[75] Inventors: Károly Lempert; Kálmán Hársanyi; Gábor Doleschall; Gyula Hornyak; József Nyitrai, all of Budapest; Károly Zauer, Szentendre; József Fetter, Budapest; Gyula Simig, Budapest; Zsuzsanna Visky née Gombos, Budapest; Gizella Barta née Szalai, Vecsés, all of Hungary

[73] Assignee: Richter Gedeon Vegyészeti Gyár Rt., Budapest, Hungary

[21] Appl. No.: 301,191

[22] Filed: Sep. 11, 1981

[30] Foreign Application Priority Data

Sep. 15, 1980 [HU] Hungary ........................ 2264/80

[51] Int. Cl.³ .................. C07D 205/08; C07D 487/04
[52] U.S. Cl. .......................... 260/239 A; 260/245.2 T
[58] Field of Search ................................ 260/239 A

[56] References Cited

U.S. PATENT DOCUMENTS 4,290,947 9/1981 Christensen ............... 260/239 A
4,322,345 3/1982 Hirata ...................... 260/239 A

OTHER PUBLICATIONS

Nippon Chemical, Chem. Abs. 98, 107076, (1981).
Watanabe, Chem. Abs. 95, 24665h, (1981).
Ogania et al., Chem. Abs. 94, 208151y, (1981).
Kano et al., Chem. Abs. 92, 198212m, (1979).
Sheehan et al., J. Amer. Chem. Soc. 22,5158.
Sheehan et al., J. Am. Chem. Soc., vol. 72, pp. 5158–5161, (1950), "A New Synthesis of Beta-Lactams".

*Primary Examiner*—Mark L. Berch
*Attorney, Agent, or Firm*—Karl F. Ross

[57] ABSTRACT

The invention relates to new heterocyclic compound containing an alkoxycarbonyl and a substituted methyl group a process for the preparation of these and analogeous compound and pharmaceutical compositions containing them.

More particularly, the invention concerns compounds of the general formula (IVa)

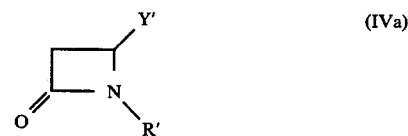

(IVa)

wherein
R′ is hydrogen, 2-ethoxycarbonylethyl, aryl or a group suitable for a temporary protection of amides and
Y′ represents a group of the formula —COOZ or —CH₂M, in which
  Z is lower alkyl and
  M is hydroxyl, halogen, cyano or a group of the formula —O—SO₂R², in which
    R² is lower alkyl or aryl, with the proviso that if R′ is phenyl, Y′ cannot stand for the group —COOC₂H₅.

The invention further relates to a process for the preparation of compounds of the general formula (IV) pg,2

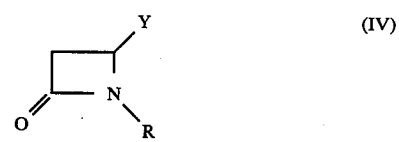

(IV)

in which R and Y are identical with R′ and Y′, respectively, except the proviso.

According to a further aspect of the invention there are provided pharmaceutical compositions, first of all with antihypoxic activity, comprising compounds of the general formula (IVa) as active ingredient.

7 Claims, No Drawings

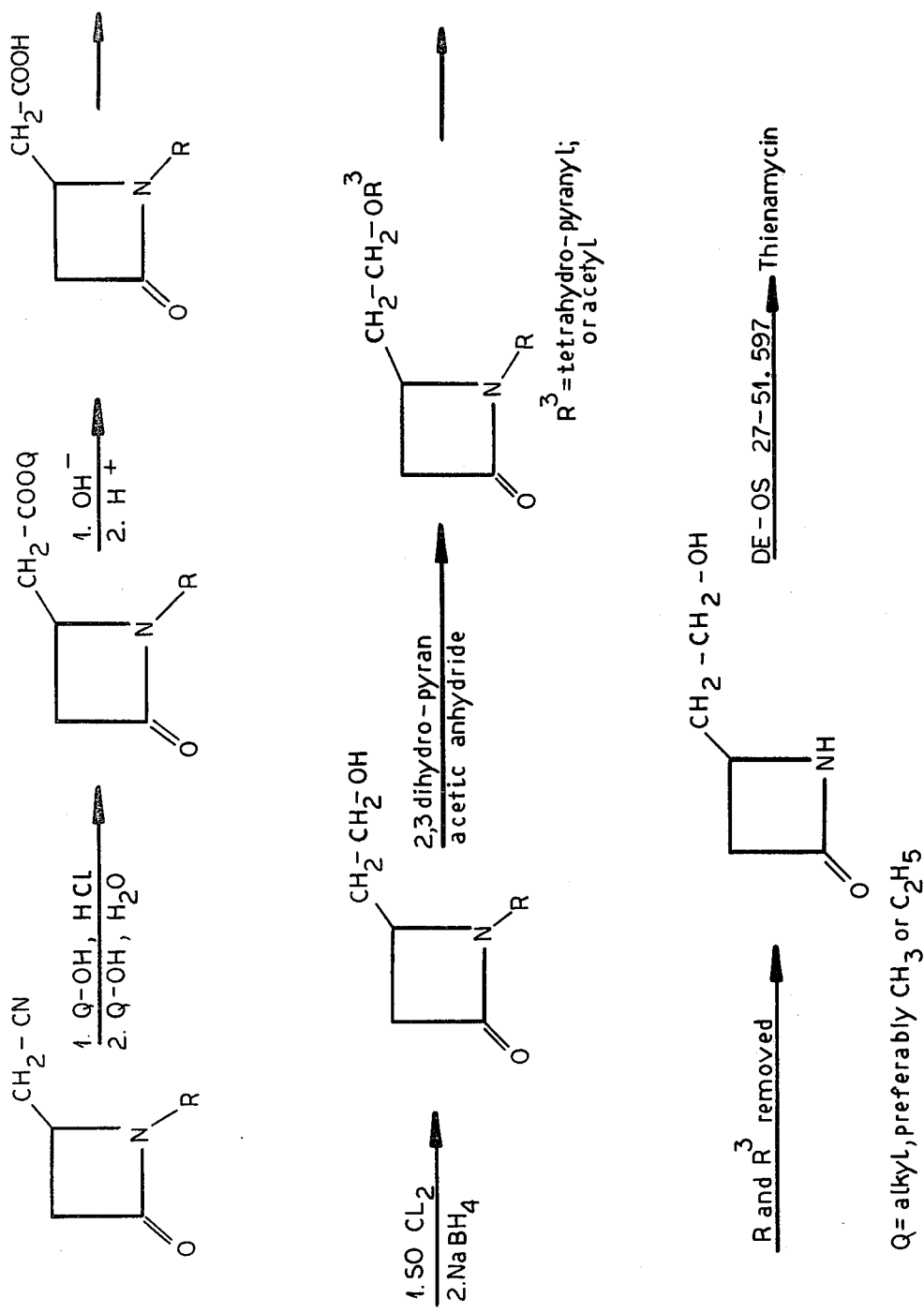

HETEROCYCLIC COMPOUNDS CONTAINING AN ALKOXYCARBONYL AND A SUBSTITUTED METHYL GROUP

The invention relates to new heterocyclic compounds containing an alkoxycarbonyl and a substituted methyl group. More particularly, the invention concerns new compounds of the formula (IVa)

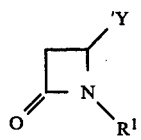

wherein
R' is hydrogen, 2-ethoxycarbonylethyl, aryl or a group suitable for temporary protection of amides and
Y' represents a group of the formula —COOZ or —CH$_2$M, in which
Z is lower alkyl and
M is hydroxyl, halogen, cyano or a group of the formula —O—SO$_2$R$^2$, in which
R$^2$ is lower alkyl or aryl, but when R' is phenyl Y' is not —COOC$_2$H$_5$.

In the definition of R' the term "aryl" relates to optionally substituted aromatic groups having 6 to 10 carbon atoms, preferably optionally substituted phenyl. The term "a group suitable for temporary protection of amides" is used to indicate conventional protecting groups suitable for the protection of amides, which can easily be removed, preferably by oxidation or reduction, preferably benzyl substituted by phenyl or one or more methoxy.

In the definition of R' and R$^2$ the term "lower alkyl" relates to straight or branched chained saturated aliphatic hydrocarbon groups having 1 to 6, preferably 1 to 4 carbon atoms, more preferably methyl.

The term "halogen" as used herein refers to chlorine, bromine, iodine or fluorine.

In the definition of R$^2$ the term "aryl" preferably refers to tolyl.

The compounds of the formula (IVa), in which R' is hydrogen, 2-ethoxycarbonylethyl or aryl, preferably optionally substituted phenyl are pharmaceutically active, more particularly show antihypoxic activity.

The compounds of the formula (IVa), in which R represents a group suitable for a temporary protection of amides, preferably benzyl substituted with phenyl or one or more methoxy are valuable intermediates in a new synthesis route to thienamycin. These new intermediates can be prepared easily and economically and may be converted into thienamycin in a multi-step synthesis illustrated on the appended drawing.

Thienamycin is a well known antibiotic having a wide spectrum of activity, which was first prepared in a microbiological way (U.S. Pat. No. 3,950,357) and then synthetically (Published German Patent Application No. 2,751,597).

The first step of the known synthesis for the preparation of thienamycin can be carried out only with a yield below 10%, and the synthesis is therefore very uneconomical.

According to a further aspect of the invention there is provided a process for the preparation of partially new compounds of the formula (IV)

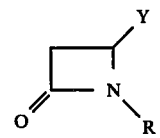

in which
R is hydrogen, 2-ethoxycarbonylethyl, aryl or a group suitable for temporary protection of amides and
Y represents a group of the formula —COOZ or —CH$_2$—M, in which
Z is lower alkyl and
M is hydroxyl, halogen, cyano or a group of the formula —O—SO$_2$R$^2$, in which
R$^2$ is alkyl or aryl.

In the definition of R and Y the terms "aryl", "a group suitable for temporary protection of amides", "lower alkyl", "halogen", and "aryl" are used in the same sense as in the definition of R' and Y', respectively.

According to the invention the compounds of the formula (IV) are prepared starting from compounds of the formula (III)

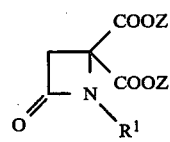

in which Z has the same meaning as defined hereinabove and R$^1$ is 2-ethoxycarbonylethyl, aryl, preferably optionally substituted phenyl or a group suitable for temporary protection of amides, preferably benzyl substituted by phenyl or optionally one or more methoxy groups.

In the definition of R$^1$ the terms "aryl" and "a group suitable for temporary protection of amides" are used in the same sense as in the definition of R' and R.

The compound of the formula (IV), in which R is phenyl and Y is a —COOZ group, in which Z is ethyl is known in the art and was prepared by J. C. Sheehan and A. K. Bose [J. Am. Chem. Soc., 72, 5158 (1950)] from a compound of the formula (III), in which R$^1$ is phenyl and Z is ethyl, under reaction conditions which are essentially different from the parameters of the reaction according to the invention. The compound was obtained as an oily liquid.

According to the invention the compounds of the formula (IV), in which R and Y are as defined above, are prepared by the following reactions:

In a first step a compound of the formula (III) (Z and R$^1$ are as defined above) is desalkoxycarbonylated to yield compounds of the formula (IV), in which R has the same meaning as R$^1$ and Y stands for a group of the formula —COOZ. The compounds are new except for the compound in which R is phenyl and Y is —COOC$_2$H$_5$.

In a second step the product of the first reaction step is reduced into a compound of the formula (IV), in which R has the same meaning as R$^1$ and Y stands for a —CH$_2$—M group, in which M is hydroxyl. The reduction is carried out with a suitable complex metal hydride. These compounds are new.

In a third reaction step the product of the second step is reacted with an alkane- or arene-sulfonic acid halide, to produce compounds of the formula (IV), in which R is identical with $R^1$ and Y stands for a group of the formula $-CH_2-O-SO_2-R^2$. All these compounds are new.

In a fourth step the product of the third reaction step is reacted with an alkali metal halide to yield compounds of the formula (IV), in which R has the same meaning as $R^1$ and Y is a $-CH_2-M$ group, in which M is halogen.

The third and fourth steps may also be combined, preferably in the presence of pyridine. In this case the product of the second step is reacted with an alkanesulfonic acid halide or arenesulfonic acid halide in the presence of a tertiary amine, at elevated temperature. The compound of the formula (IV) obtained, in which R is identical with $R^1$ and Y stands for a group $-CH_2-O-SO_2-R^2$, is an intermediate. The hydrogen halide obtained as a by-product forms a salt with the tertiary amine and from the hydrogen halide component of the salt obtained the halogen atom replaces the group $-O-SO_2-R^2$. As a result of this reaction a compound of the formula (IV), in which R has the same meaning as $R^1$ and Y represents a $-CH_2-M$ group, in which M is halogen, is obtained.

The product of the fourth step, which may be carried out separately or combined with the third step, is reacted with an alkali metal cyanide to yield a new compound of the formula (IV), in which R is identical with $R^1$, Y stands for a $-CH_2-M$ group, wherein M is cyano.

Compounds of the formula (IV), in which R is hydrogen are prepared from compounds of the formula (IV), in which R is a group suitable for a temporary protection of amides and Y is a $-COOZ$ or $-CH_2-M$ group, wherein M is $-O-SO_2-R^2$, by eliminating the protecting group. The protecting group may be split off by oxidation or reduction. The dimethoxybenzyl protecting group is eliminated by an oxidizing agent of peroxidisulfate type. In this way a compound of the formula (IV), in which R is hydrogen, Y is $-COOZ$ or $-CH_2-O-SO_2-R^2$ is obtained. From the latter compounds further compounds of the formula (IV), in which R is hydrogen, Y is $-CH_2M$, in which M is halogen, can also be prepared.

Accordingly, according to the invention compounds of the formula (IV), in which R, Y, M, Z and $R^2$ are as defined hereinabove, are prepared by reacting a compound of the formula (III), in which Z and $R^1$ are as defined above, with an alkali metal halide in pyridine or a similar solvent or in aqueous dimethyl sulfoxide, and isolating a compound of the formula (IV) obtained, in which R has the same meaning as defined above, except hydrogen, and Y represents a $-COOZ$ group, in which Z is as defined above, or if desired, reacting it with a suitable complex metal hydride, preferably alkali metal tetrahydrodiborate, and isolating a compound of the formula (IV) obtained, in which R is as defined above, except hydrogen, Y is $-CH_2-M$, in which M is hydroxyl, or if desired, reacting this compound with a lower alkane- or arenesulfonic acid halide, preferably mesyl or tosyl halide, and isolating a compound of the formula (IV) obtained, in which R is as defined above, except hydrogen, Y stands for a group $-CH_2-M$, in which M represents a group $-O-SO_2-R^2$, in which $R^2$ has the same meaning as hereinbefore defined; or (a) if desired, reacting this compound with an alkali metal halide, or optionally with a hydrogen halide salt of a tertiary amine, and isolating a compound of the formula (IV) obtained, in which R is as defined above, except hydrogen, Y is a group $-CH_2-M$, in which M is halogen, or if desired, reacting same with an alkali metal cyanide, and isolating a compound of the formula (IV) obtained, in which R has the same meaning as defined above and Y is a $-CH_2-M$ group, in which M is cyano; or (b) if desired, splitting off the protecting group from a compound of the formula (IV), in which R is a group suitable for a temporary protection of amides and Y is a $-COOZ$ group, in which Z has the same meaning as defined above, and Y stands for a $-COOZ$ group, in which Z has the same meaning as defined above, or Y stands for a $-CH_2-M$ group, in which M is a $-O-SO_2-R^2$ group, wherein $R^2$ has the same meaning as defined above, by oxidation or reduction, if R=methyoxy-substituted benzyl, preferably by a compound of peroxidisulfate type, and isolating the compound of formula (IV) obtained, in which R is hydrogen, Y is a $-COOZ$ group, or a $-CH_2-M$ group, in which M is $-O-SO_2-R^2$, or if desired, reacting a compound of the formula (IV) obtained, in which Y represents a $-CH_2-O-SO_2-R^2$ group with an alkali metal halide or optionally with a hydrogen halide salt of a tertiary amine, and isolating a compound of the formula (IV) obtained, in which R is hydrogen and Y is a $-CH_2-M$ group, in which M is halogen from the reaction mixture.

In the process according to the invention compounds of the formula (III) are employed as starting compounds. Of the compounds having the formula (III) there is a single compound known in the art, the preparation of which is disclosed in Chem. Soc. 72, 5158 (1950).

The new compounds of the formula (III) are synthesized as follows: Compounds of the formula (I)

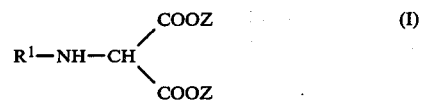

wherein $R^1$ and Z have the same meaning as hereinbefore defined, are reacted with haloacetic acid derivatives, which are suitable for acylation, e.g. with a haloacetic acid halide or anhydride or with haloacetic acid per se, in the presence of a carboxylic acid activator, to give compounds of the formula (II)

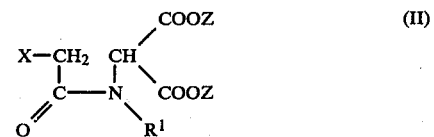

in which $R^1$ and Z are as defined above and X is halogen.

Compounds of the formula (II) are converted into compounds of the formula (III) in the presence of an acid binding agent.

The preparation of new compounds of the formula (III) is illustrated by Examples 1, 2, 3, 7, 8, 9, 18, 19, 20, 30, 31 and 32.

The compounds of the formula (III) are first reacted with alkali metal halides, preferably with sodium or lithium chloride in the presence of pyridine, quinoline, their homologs or optional mixtures of these compounds, or dimethylsulfoxide and water. In this way compounds of the formula (IV), in which R has the same meaning as $R^1$ (i.e. R may stand for the groups identified hereinbefore, except hydrogen) and Y is —COOZ, in which Z is a lower alkyl, preferably methyl or ethyl group, are obtained.

The compounds of the formula (IV) obtained if desired, can be converted into other compounds of the formula (IV). By reduction compounds of the formula (IV), in which R has the above meaning and Y stands for a group —CH$_2$—M, in which M is hydroxyl are obtained. As a reducing agent a suitable complex metal hydride, preferably alkali metal tetrahydrodiborate is employed. The reaction can be carried out in a solvent, such as a lower alkanol, preferably methanol or aqueous tetrahydrofurane.

If desired, the compounds of the formula (IV) obtained by reduction can be reacted with lower alkanesulfonic acid halides, preferably mesyl chloride or arehesulfonic acid halides, preferably p-toluenesulfonic acid chloride to yield compounds of the formula (IV) in which Y stands for a group —CH$_2$—M, in which M represents an —O—SO$_2$—R$^2$ group (the definition of R does not change). The reaction is preferably performed in an inert organic solvent, in the presence of an organic base, or in pyridine or a homolog thereof, preferably pyridine, under cooling.

If desired, the compounds of the formula (IV), in which Y represents a —CH$_2$—M substituent (M=—O—SO$_2$—R$^2$) are reacted with alkali metal halides, preferably sodium iodide, to give compounds of the formula (IV), in which Y represents a —CH$_2$—M substituent, wherein M is halogen. preferably iodine. The reaction is carried out in an organic solvent, preferably acetone.

Alternatively, a compound of the formula (IV), in which Y stands for a group —CH$_2$—M, in which M is hydroxyl may be reacted with a lower alkanesulfonic acid halide, preferably mesyl chloride or arenesulfonic acid halide, preferably p-toluene-sulfonic acid chloride, in the presence of a tertiary amine, preferably pyridine or triethyl amine, at elevated temperature. In this way a compound of the formula (IV), in which Y represents a —CH$_2$—M group, in which M is halogen, preferably chlorine (R has the same meaning as before) is obtained.

If a compound of the formula (IV), in which Y stands for a —CH$_2$—M group, in which M is halogen and R has the same meaning as hereinbefore defined, except hydrogen, prepared according to any one of the preceding reactions, is reacted with an alkali metal cyanide, a corresponding compound of the formula (IV), in which M is cyano (R remains unchanged) is obtained. The reaction is preferably accomplished in a dipolar aprotic solvent, preferably dimethyl formamide, at room temperature.

From the compounds of the formula (IV), in which Y stands for a —COOZ group of —CH$_2$—M group, wherein M is a group —O—SO$_2$—R$^2$ and R stands for a group suitable for a temporary protection of amides, the protecting group can be eliminated. The elimination may be performed oxidatively or reductively.

If the protecting group is a dimethoxybenzyl group, it can be split off oxidatively, preferably by means of a compound of peroxidisulfate type, preferably potassium or sodium peroxidisulfate (Na$_2$S$_2$O$_8$).

The reaction is carried out in the presence of a buffer of pH 7 and water and an organic solvent.

Pharmaceutical compositions containing an effective amount of compounds of the formula (IVa) are also within the scope of the invention. They contain the active ingredient in association with conventional, inert pharmaceutical carriers and optionally further additives.

Further details of the invention are illustrated by the following, non-limiting Examples.

EXAMPLE 1

Diethyl-N-(2-ethoxycarbonylethyl)-amino-malonate hydrochloride (a) 41.4 g. (39 ml., 0.2 moles) of ethyl 2-(benzylamino)-propionate and 23.9 g. (117 ml., 0.1 moles) of diethyl bromomalonate are allowed to stand at room temperature for 4 days. After several hours precipitation of a crystalline substance can be observed. The thick crystalline mass is triturated with 200 ml. of ether. filtered and washed with ether. 28 g. (97%) of ethyl 2-(benzylamino)-propionate, i.e. the excess of the starting material can be isolated in the form of hydrobromide salt. The filtrate is evaporated in vacuo, the residue is dissolved in n-pentane, the insoluble materials are filtered off and the solution is evaporated. 32. g. (87%) of diethyl-N-benzyl-N-(2-ethoxycarbonylethyl)-amino-malonate are obtained as an oily product. IR spectrum (film): 2950, 1760, 1740, 1720 cm$^{-1}$. Upon addition of hydrochloric acid in ether the corresponding hydrochloride salt is obtained, melting at 160° C.

(b) 55 g. (0.15 moles) of diethyl N-benzyl-N-(2-ethoxycarbonylethyl)-amino-malonate prepared according to Example 1 (a) are dissolved in 400 ml. of ethanol and subjected to hydrogenation in the presence of 22 g. of palladium-on-charcoal. Hydrogenation is carried out at 40° to 50° C. for 3 hours and at room temperature for 5 to 6 hours. After filtering off the catalyst the solution is evaporated in vacuo. 37 g. (89%) of diethyl N-(2-ethoxycarbonylethyl)-amino-malonate are obtained. By crystallization from ethanol saturated with hydogen chloride gas upon addition of ether the corresponding hydrochloride is obtained. Yield. 38.3 g. (82%) of diethyl N-(2-ethoxycarbonylethyl)-amino-malonate hydrochloride, melting at 156° to 157° C. (Ethanol/ether).

Analysis for $C_{12}H_{22}NO_6Cl$: Calculated: Cl 11.37%, N 4.49%; Found: Cl 11.02%, N 4.37%.

IR spectrum (film): 3300, 2950, 2850 v, 1750 to 1730 cm$^{-1}$.

EXAMPLE 2

Diethyl N-(2-ethoxycarbonylethyl)-N-(chloroacetyl)-amino-malonate

To a suspension of 14 g. (0.045 moles) of diethyl N-(2-ethoxycarbonylethyl)-amino-malonate hydrochloride prepared according to Example 1b) in 150 ml. of dry benzene 5.65 g. (4 ml., 0.05 moles) of chloroacetyl chloride are added with stirring. The mixture is boiled for 5 hours. The solution is evaporated in vacuo, the evaporation residue is triturated with 50 ml. of hexane, hexane is decanted and the same procedure is repeated two more times. The oily product is dried over sodium hydroxide in a vacuum desiccator. 13.6 g. (86%) of the named compound are obtained.

IR spectrum (film): 2920, 1740–1710, 1660–1645 cm$^{-1}$.

$^1$H-NMR spectrum (CDCl$_3$): 1.15–42 m (9H); 2.70 t (2H), 3.8 t (2H); 4.0–4.45 m (8H); 5.08 s (1H).

EXAMPLE 3

Diethyl 1-(2-ethoxycarbonylethyl)-4-oxo-2,2-azetidine-dicarboxylate

To a solution of 19.7 g. (0.056 moles) of diethyl N-(2-ethoxycarbonylethyl)-N-(chloroacetyl)-amino-malonate prepared according to Example 2 in 200 ml. of dry benzene 13 ml. (9.5 g., 0.095 moles) of triethyl amine are added and the reaction mixture is boiled for 3 hours. The solution is shaken with two 50-ml. portions of a 5% aqueous hydrochloric acid solution and subsequently with 50 ml. of water, the benzene phase is dried with magnesium sulfate, filtered and the filtrate is evaporated in vacuo. 16.5 g. (93%) of the named compound are obtained. The product is practically uniform and can be used for further conversions without further purification.

By vacuum distillation of 16.5 g. of the above crude product 13.2 g. (75%) of a pale yellow oil are obtained, boiling at 166° to 168° C./0.6 mmHg.

Analysis for $C_{14}H_{21}NO_7$ (315.3): Calculated: C 53.33%, H 6.71%, N 4.44%; Found: C 53.33%, H 6.56%, N 4.34%.

IR spectrum (film): 2950, 1765, 1740 cm$^{-1}$:

$^1$H-NMR spectrum (CDCl$_3$): δ1.1–1.55 m (9H); 2.7 t (2H); 3.28 s (2H); 3.62 t (2H); 5.9–6.5 m(6H).

EXAMPLE 4

Ethyl 1-(2-ethoxycarbonylethyl)-4-oxo-2-azetidine-carboxylate

To a solution of 9.5 g. (30 mmoles) of crude diethyl 1-(2-ethoxycarbonylethyl)-4-oxo-2,2-azetidine-dicarboxylate in 10 ml. of dimethyl sulfoxide 2.11 g. (36 mmoles) of sodium chloride and 1.1 ml. (60 mmoles) of water are added and the mixture is stirred for 9 hours at an oil bath of 180° C. The reaction mixture is poured on 200 ml. saturated aqueous hydrochloric acid solution and extracted with five 60-ml. portions of ether. The ethereal extract is dried with magnesium sulfate, filtered and the filtrate is evaporated in vacuo.

4.5 g. (61%) of the named compound are obtained as a pale yellow oil. The obtained crude product can be subjected to further transformations without purification. By distillation at 145° C., under a pressure of 0.6 mmHg. 3.15 g. (43%) of a purified product are obtained.

Analysis for $C_{11}H_{17}NO_5$ (243.3): Calculated: C 54.30%, H 7.04%, N 5.75%; Found: C 54.17%, H 6.97%, N 5.96%.

$^1$H-NMR spectrum (CDCL$_3$): δ1.25 t (3H); 1.30 t (3H); 2.50 t (2H); 3.05 m (2H); 3.55 m (2H); 5.9–6.4 m (5H).

EXAMPLE 5

1-(2-Ethoxycarbonylethyl)-4-(hydroxymethyl)-2-azetidinone 4.5 g. (18.5 mmoles) of ethyl 1-(2-ethoxycarbonylethyl)-4-oxo-2-azetidine-carboxylate prepared according to Example 4 are dissolved in 20 ml. of dry ethanol, whereupon 1.4 g. (37 mmoles) of sodium tetrahydroborate(III) are added to the solution at 0° C., with stirring. The reaction mixture is stirred for an additional hour, and is then evaporated in vacuo, at room temperature. The residue is dissolved in 20 ml. of saturated aqueous hydrochloric acid solution and the pH of the solution is adjusted to 6.5 by addition of a 5% aqueous hydrochloric acid solution. The mixture is extracted with three 30-ml. portions of chloroform, dried with magnesium sulfate and filtered. The remaining solution is evaporated in vacuo. 3.1 g. (83%) of the named compound are obtained.

EXAMPLE 6

1-(2-Ethoxycarbonylethyl)-4-(mesyloxymethyl)-2-azetidinone 1.6 g. (8 mmoles) of 1-(2-ethoxycarbonylethyl)-4-(hydroxymethyl)-2-azetidinone prepared according to Example 5 are dissolved in 50 ml. of dry benzene, whereupon 2.2 ml. (1.16 g, 16 mmoles) of triethylamine are added to the solution, followed by a dropwise addition of 1.2 ml. (1.8 g., 16 mmoles) of mesyl chloride at 0° C., with stirring. After 30 minutes the salt is filtered off and the filtrate is evaporated in vacuo. The evaporation residue is dissolved in 50 ml. of chloroform, the solution is shaken with two 10-ml. portions of a 10% aqueous sodium carbonate solution and subsequently with three 10-ml. portions of water. The chloroform phase is dried over magnesium sulfate, filtered and the filtrate is evaporated. 1.9 g. (85%) of the named compound are obtained.

$^1$H-NMR (CDCl$_3$): δ1.35 t (3H); 2.6 t (2H); 3.10 s (3H); 2.95 m (2H); 3.9–4.65 m (5H).

EXAMPLE 7

Diethyl N-(2,4-dimethoxybenzyl)-amino-malonate (a) 50 g. (0.30 moles) of 2,4-dimethoxy-benzaldehyde and 34.4 ml. (33.6 g., 0.31 moles) of benzylamine are boiled in 300 ml. of dry toluene, in the presence of 1 g. of p-toluenesulfonic acid for 8 hours, while water formed in continuously eliminated by a water separator. Toluene is then distilled off. The obtained oil is dissolved in 120 ml. of dioxane and 3.2 g. of sodium tetrahydridoborate(III) are added, followed by the addition of a further 3.2 g. portion of the same compound after stirring for 2 hours.

The reaction mixture is allowed to stand for 3 days, whereupon it is diluted with 400 ml. of water. The obtained oil is extracted with ether, dried with magnesium sulfate, filtered and the filtrate is evaporated to half of its original volume. Thereafter hydrochloric acid in ethanol is added to the ethereal solution slowly, under cooling with ice water.

59. g. (67%) of benzyl (2,4-dimethoxybenzyl)amine-hydrochloride are obtained, melting at 156° to 157° C. (ethyl acetate).

Analysis for $C_{16}H_{20}ClNO_2$ (293.78):

Calculated: C 65.41%, H 6.86%, Cl 12.07%, N 4.77%; Found: C 65.63%, H 7.30%, Cl 11.69%, N 4.72%.

(b) From the product of Example 7(a) the corresponding base is set free, whereupon the obtained 175 g. (0.68 moles) of benzyl (2,4-dimethoxybenzyl)amine are stirred with 89.6 g. (0.38 moles, 64 ml.) of diethyl bromomalonate at room temperature until the reaction mixture solidifies. The solidified mixture is triturated with about one liter of ether and the crystalline precipitate obtained is filtered off. (In this way the excess of starting material can be recovered in the form of hydrobromide with a yield of about 95%). The filtrate is evaporated and the residual oil is triturated with ethanol.

114.5 g. (81%) of diethyl N-benzyl-N-(2,4-dimethoxybenzyl)-amino-malonate are obtained, melting at 62 to 63° C. (ethanol).

Analysis for $C_{23}H_{29}NO_6$ (415.47): Calculated: C 66.49%, H 7.04%, N 3.37%; Found: C 66.58%, H 7.09%, N 3.43%.

IR spectrum (KBr): 1750/1725 cm$^{-1}$, d (c) 61.7 g. (0.149 moles) of diethyl N-benzyl-N-(2,4-dimethoxybenzyl)-amino-malonate prepared according to Example 7(b) are hydrogenated in the presence of 20 g. of palladium-on-charcoal, in 500 ml. of ethanol, under atmospheric pressure. The catalyst is filtered off and the filtrate is evaporated. 47.1 g. (97%) of diethyl N-(2,4-dimethoxybenzyl)-amino-malonate are obtained. If desired, the product is converted into the corresponding hydrochloride, which melts at 122° to 124° C. (EtOAc).

Analysis for $C_{16}H_{24}ClNO_6$ (361.82): Calculated: C 53.11%, H 6.69%, Cl 9.80%, N 3.87%; Found: C 52.51%, H 6.77%, Cl 10.30%, N 4.09%.

IR spectrum (film): 3250, 2900, 2850, 1730, 1720 cm$^{-1}$.

$^1$H-NMR spectrum (CDCl$_3$): δ1.3 t (6H); 3.78 s (3H); 3.82 s (3H); 4.21 q (4H); 6.20 s (2H); 6.4–6.6 m (2H)+7.3–7.55 m (1H); 7.7 sz s (1H).

EXAMPLE 8

Diethyl-N-(2,4-dimethoxybenzyl)-N-(chloroacetyl)-amino-malonate 47 g. (0.144 moles) of diethyl N-(2,4-dimethoxybenzyl)-amino-malonate in 200 ml. of dry benzene are boiled with 13.8 ml. (19.6 g., 0.173 moles) of chloroacetyl choride for 3.5 hours. Benzene is distilled off and the oily residue is recrystallized from about 100 ml. of ethanol. The named compound is obtained with a yield of 66%. Melting point: 83° to 84° C. (ethanol).

Analysis for $C_{18}H_{24}ClNO_7$ (401.84): Calculated: C 53.80%, H 6.02%, Cl 8.82%, N 3.49%; Found: C 53.63%, H 6.26%, Cl 8.79%, N 3.56%.

IR spectrum (KBr): 2920, 1755, 1680 cm$^{-1}$.

$^1$H-NMR spectrum (CDCl$_3$): δ1.2 t (6H); 3.72 s (6H); 4.08 q (4H); 4.17 s (2H); 4.56 s (2H); 4.95 s (1H); 6.2–6.6 m (2H)+6.95–7.25 m (1H).

EXAMPLE 9

Diethyl 1-(2,4-dimethoxybenzyl)-4-oxo-2,2-azetidine-dicarboxylate 35 g. (0.087 moles) of diethyl N-(2,4-dimethoxybenzyl)-N-(chloroacetyl)-amino-malonate prepared according to Example 8 are boiled with 15.9 ml. (11.4 g., 0.113 moles) of triethylamine in 200 ml. of dry benzene for 8 hours. The mixture is shaken with 100 ml. of water, 100 ml. of dilute hydrochloric acid and again with 100 ml. of water. The benzene phase is dried with magnesium sulfate, filtered and the filtrate is evaporated. 28.4 g. (89%) of the named compound are obtained, boiling at 175° to 180° C./0.1 mmHg.

Analysis for $C_{18}H_{23}NO_7$ (365.38): Calculated: C 59.17%, H 6.34%, N 3.83%; Found: C 59.24%, H 6.24%, N 3.54%.

IR spectrum (KBr): 2900, 1760–1720 cm$^{-1}$.

$^1$H-NMR spectrum (CDCL$_3$): δ1.15 t (3H); 1.25 t (3H); 3.25 s (2H); 3.7 s (6H); 3.8–4.25 m (4H); 4.50 s (2H); 6.3 m (2H)+7.0 d (1H).

EXAMPLE 10

Ethyl 1-(2,4-dimethoxybenzyl)-4-oxo-2-azetidine-carboxylate 66.2 g. (0.18 moles)(of diethyl 1-(2,4-dimethoxybenzyl)-4-oxo-2,2-azetidine-carboxylate prepared according to Example 9 in 70 ml. of dimethyl sulfoxide are stirred in the presence of 12.7 g. (0.22 moles) of sodium chloride and 6.5 ml. (0.36 moles) of water, at an oil bath of 170° to 180° C. for 6 hours. The mixture is poured onto 500 ml. of a saturated aqueous sodium chloride solution, shaken with five 100-ml. portions of ethyl acetate, the organic phase is dried with magnesium sulfate, filtered and from the filtrate ethyl acetate is distilled off. 47.6 g. (90%) of the title compound are obtained, boiling at 170° to 176° C./mmHg.

Analysis for $C_{15}H_{19}NO_5$ (293.32):

Calculated: C 61.42%, H 6.53%, N 4.77%; Found: C 61.25%, H 6.87%, N 4.58%.

IR spectrum (film): 2900, 1750 to 1725 cm$^{-1}$.

EXAMPLE 11

1-(2,4-Dimethoxybenzyl)-4-(hydroxymethyl)-2-azetidinone 47.6 g. (0.162 moles) of ethyl-1-(2,4-dimethoxybenzyl)-4-oxo-2-azetidine-carboxylate prepared according to Example 10 are reacted with 12.4 g. (0.327 moles) of sodium tetrahydrido-borate(III), in 200 ml. of methanol, under outer cooling with ice water for about half an hour. The solution is neutralized with a dilute aqueous hydrochloric acid solution and the oil precipitated from the aqueous mixture is shaken with five 50-ml. portions of ethyl acetate.

The ethyl acetate phase is dried with magnesium sulfate, filtered and the filtrate is evaporated. 39.1 g. (96%) of the named compound are obtained.

IR spectrum (film): 3350 2900, 1740–1700 cm$^{-1}$.

$^1$H-NMR spectrum (CDCl$_3$): δ2.1 sz s (1H); 2.85 m (2H); 3.65 (2H); 3.82 s (3H); 3.85 s (3H); 4.05 m (1H); 6.38 s (2H); 6.55 m (2H)+7.25 d (1H).

EXAMPLE 12

1-(2,4-Dimethoxybenzyl)-4-(mesyloxymethyl)-2-azetidinone

To a solution of 39.1 g. of 1-(2,4-dimethoxybenzyl)-4-(hydroxymethyl)-2-azetidinone prepared according to Example 11 in 100 ml. of pyridine 15.3 ml. (23.6 g., 0.206 moles) of mesyl chloride are added dropwise, whereupon the mixture is stirred until the reaction is complete (2 to 3 hours). The mixture is poured onto 500 ml. of water. The precipitated oil slowly crystallizes. 37.5 g. (73%) of the named compound are obtained, melting at 71° to 72° C. (ether).

Analysis for $C_{14}H_{19}NO_6S$ (329.36):

Calculated: C 51.05%, H 5.81%, N 4.25%, S 9.74%; Found: C 51.19%, H 6.07%, N 4.19%, S 9.93%.

IR spectrum (KBr): 1735 cm$^{-1}$.

EXAMPLE 13

1-(2,4-Dimethoxybenzyl)-4-(iodomethyl-2-azetidinone 37.5 g. (0.107 moles) of 1-(2,4-dimethoxybenzyl)-4-(mesyloxymethyl)-2-azetidinone in 250 ml. of dry acetone are boiled with 56.3 g. (0.376 moles) of sodium iodide for 8 hours. To the mixture a further 18.8-g. portion (0.125 moles) of sodium iodide are added, and its is boiled for another 8 hours. The mixture is evaprated to dryness on a water bath of 50° C., in vacuo, the residue is triturated with 100 ml. of water and the oil obtained is extracted with 100 ml. of dichloromethane. The combined dichloromethane extracts are dried with magnesium sulfate, filtered and the filtrate is evaporated. 40.3 g. (98%) of the named compound are obtained.

IR spectrum (film): 2920, 1750 cm$^{-1}$.

EXAMPLE 14

4-(Cyanomethyl)-1-(2,4-dimethoxybenzyl)-2-azetidinone

A solution of 1.2 g. (3.3 mmoles) of 1-(2,4-dimethoxybenzyl)-4-(iodomethyl)-2-azetidinone prepared according to Example 13 in 5 ml. ofdimethyl formamide is stirred with 0.35 g. (7 mmoles) of sodium cyanide for 48 hours, at room temperature. The solution is then poured onto 30 ml. of water and extracted with five 20-ml. portions of ether. The ethereal solution is dried with magnesium sulfate, decolored with activated carbon, filtered and the filtrate is evaporated in vacuo. 0.6 g. (70%) of the named compound are obtained.

Analysis for $C_{14}H_{16}N_2O_3$ (260.3):
Calculated: N 10.76%; Found: N 10.71%.
IR spectrum (film): 2920, 2270, 1750 cm$^{-1}$.

EXAMPLE 15

4-(Mesyloxymethyl)-2-azetidinone 16 g. (48.6 mmoles) of 1-(2,4-dimethoxybenzyl)-4-(mesyloxymethyl)-2-azetidinone, 26.3 g. (97.4 mmoles) of potassium peroxidisulfate and 34.5 g. (193 mmoles) of disodium hydrogenphosphate×2 $H_2O$ are boiled in a mixture of 160 ml. of water and 240 ml. of acetonitrile for 3 hours. The biphase mixture is separated, the aqueous phase is shaken with five 100-ml. portions of ether. The combined organic phase is dried with magnesium sulfate, filtered and the filtrate is evaporated. The oily residue is crystallized from 50 ml. of ethanol. 4.6 g. (53%) of the compound named are obtained, melting at 117° to 118° C. (ethanol).

IR spectrum (KBr): 3210, 1740-1710 cm$^{-1}$.
$^1$H-NMR spectrum (DMSO-d$_6$): δ2.75 m (1H); 2.9 m (1H); 3.22 m (3H); 3.85 m (1H); 4.3 m (2H); 8.15 sz s (1H).

EXAMPLE 16

4-(Iodomethyl)-2-azetidinone 0.6 g. (3.35 mmoles) of 4-(mesyloxymethyl)-2-azetidinone in 5 ml. of dry acetone are boiled with 0.88 g. (5.87 mmoles) of sodium iodide for 5 hours, with stirring. Thereafter 0.2 g. (1.33 mmoles) of sodium iodide are added to the mixture, which is then boiled for another five hours. 20 ml. of water are added to the reaction mixture and it is shaken with five 50-ml. portions of ether. The organic phase is dried with magnesium sulfate, filtered and the filtrate is evaporated. 0.95 g. (91%) of the compound named are obtained, melting at 110° to 111° C. after crystallization from ethyl acetate.

$^1$H-NMR spectrum (CDCl$_3$): δ2.67 ddd (1H); 3.11 ddd (1H); 3.32 d (2H); 3.88 m (1H); 6.4 sz s (1H).
$^{13}$C-NMR spectrum (DMSO-d$_6$): 11.3; 44.3; 47.9; 166.2.

EXAMPLE 17

Ethyl 4-oxo-2-azetidine-carboxylate 6 g. (20.5 mmoles) of ethyl 1-(2,4-dimethoxybenzyl)-4-oxo-2-azetidine-carboxylate prepared according to Example 10, 11 g. (41 mmoles) of potassium peroxidisulfate and 14.5 g, (82 mmoles) of disodium hydrogenphosphate×2H$_2$O are boiled in a mixture of 60 ml. of water and 90 ml. of acetonitrile for 6 hours. The biphase reaction mixture is separated, the aqueous phase is shaken with 100 ml. of benzene and the combined organic phase is extracted with three 30-ml. portions of a saturated aqueous sodium chloride solution. The organic phase is dried with magnesium sulfate, filtered and the filtrate is evaporated. The obtained oily product is subjected to column chromatography (Kieselgel 60, 0.063–0.200 mm., benzene followed by a 99:1 mixture of benzene and acetone). 1.21 g. (41%) of the named compound are obtained.

IR spectrum (film): 3250, 2930, 1740 cm$^{-1}$.
$^1$H-NMR spectrum (CDCl$_3$): δ1.3 t (3H); 3.15 m (2H); 4.15 m (1H); 4.22 q (2H); 6.6 sz s (1H):

EXAMPLE 18

Diethyl benzylamino-malonate hydrochloride 59.2 g. (41.2 ml., 0.199 moles) of diethyl bromomalonate and 22.5 g. (31.5 ml., 0.225 moles) of triethyl amine are admixed and to the mixture 24 g. (24.3 ml., 0.207 moles) of benzylamine are added with intensive outer cooling with ice water and vigorous stirring. A thick mixture is obtained, which is difficult to stir. After 1.5 hours stirring the mixture is triturated with 100 ml. of ether, the precipitated crystals are filtered off and to the filtrate hydrochloric acid in ethanol is added dropwise. The precipitate is filtered off and washed with ether to yield 23 g. (31%) of the compound named, melting at 146° to 148° C. (decomposition).

EXAMPLE 19

Diethyl-N-benzyl-N-(chloroacetyl)-amino-malonate 30.1 g. (0.1 moles) of diethyl benzylamino-malonate hydrochloride prepared according to Example 18 and 9.6 ml. (13.6 g., 0.12 moles) of chloroacetal chloride are boiled for 1 hour. Benzene is distilled off. The residual oil is triturated with petroleum ether to yield 32.5 g. (95%) of the compound named, which melts at 53° to 54° C. after crystallization from a mixture of either and petroleum ether.

Analysis for $C_{16}H_{20}CiNO_5$ (341.85):
Calculated: C 56.21%, H 5.89%, N 4.10%, Cl 10.37%;
Found: C 56.13%, H 5.94%, N 3.94%, Cl 10.20%.
IR spectrum (KBr): 2950, 1760, 1740, 1685 cm$^{-1}$.
$^1$H-NMR spectrum (CDCl$_3$): δ1.2 t (6H); 4.05 s (2H); 4.15 q (4H); 4.75 s (2H); 5.35 s (1H); 7.28 s (5H).

EXAMPLE 20

Diethyl 1-benzyl-4-oxo-2,2-azetidine-dicarboxylate 34.1 g. (0.1 moles) of diethyl N-benzyl-N-(chloroacetyl)-amino-malonate prepared according to Example 19 and 18.2 ml. (13.2 g., 0.13 moles) of triethyl amine in 100 ml. of benzene are stirred at room temperature for 8 hours. The mixture is shaken with 100 ml. of water, 50 ml. of a 10% aqueous hydrochloric acid solution and again with 100 ml. of water. The organic phase is dried with magnesium sulfate, filtered and from the filtrate benzene is distilled off. The oily residue is distilled at 149° to 150° C., under a pressure of 0.1 mmHg. 23 g. (75%) of the named compound are obtained.

Analysis for $C_{16}H_{19}NO_5$ (305.33);
Calculated: C 62.94%, H 6.27%, N 4.59%;

Found: C 63.29%, H 6.75%, N 4.83%.

IR spectrum (film): 2950, 1760–1730 cm$^{-1}$.

$_1$H-NMR spectrum (CDCl$_3$): δ1.15 t (6H); 3.38 s (2H); 4.0 q (4H); 4.6 s (2H); 7.25 s (5H).

EXAMPLE 21

Ethyl 1-benzyl-4-oxo-2-azetidine-carboxylate 20 g. (0.065 moles) of diethyl 1-benzyl-4-oxo-2,2-azetidine-carboxylate prepared according to Example 20 in 30 ml. of diethyl sulfoxide, in the presence of 4.95 g. (0.084 moles) of sodium chloride and 2.35 ml. (0.13 moles) of water are stirred on an oil bath of 170° to 180° C. for about 6 hours. The reaction mixture is poured onto a saturated, aqueous sodium chloride solution, extracted with two 30-ml. portions of ether and the ethereal solution is dried with magnesium sulfate, filtered and the filtrate is evaporated. 11.4 g. (75%) of the named compound are obtained, boiling at 156° to 160° C./0.2 mmHg.

Analysis for C$_{13}$H$_{15}$NO$_3$ (233.26): Calculated: N 6.00%; Found: N 6.01%.

$^1$H-NMR spectrum (CDCl$_3$): δ1.25 t (3H); 3.1 m (2H); 3.9 m (1H); 4.18 q (2H); 4.20 d (1H); 4.65 (1H); 7.3 s (5H).

EXAMPLE 22

1-Benzyl-4-(hydroxymethyl)-2-azetidinone

To a solution of 8.5 g (0.0365 moles) of ethyl 1-benzyl-4-oxo-azetidine-carboxylate in 30 ml. of methanol 2.65 g. (0.07 moles) of sodium tetrahydro-burate(III) are added with outer cooling with ice water, with stirring. The reaction mixture is stirred for one hour, whereupon its pH is adjusted to 6 with a 10% aqueous hydrochloric acid solution. Methanol is distilled off in vacuo. To the mixture obtained 50 ml. of a saturated, aqueous sodium chloride solution are added, whereupon it is extracted with three 30-ml. portions of chloroform. The organic phase is dried with magnesium sulfate, filtered and the filtrate is evaporated. The residual oil is triturated with petroleum ether and treated with several drops of ethanol to yield 6 g. (86%) of the named compound in crystalline form. Melting point: 94° C. (ethyl acetate).

Analysis for C$_{11}$H$_{13}$ NO$_2$ (191.22): Calculated: C 69.09%, H 6.85%, N 7.33%; Found: C 68.32%, H 6.41%, N 6.98%.

$^1$H-NMR spectrum (CDCl$_3$): δ2.55 m (1H); 2.85 m (2H); 3.6 sz s (2H); 4.05 m (1H); 4.3 and 4.4 AB q (2H); 7.25 s (5H).

EXAMPLE 23

1-Benzyl-4-(mesyloxymethyl)-2-azetidinone

To a solution of 2 g. (0.011 moles) of 1-benzyl-4-(hydroxymethyl-2-azetidinone prepared according to Example 22 in 13 ml. of pyridine 0.96 ml. (1.44 g., 0.013 moles) of mesyl chloride are added dropwise, with outer cooling with ice waer, with stirring. After stirring for 2 hours the mixture is poured onto 130 ml. of water and the crystalline precipitate is filtered off. 2 g. (71%) of the named compound are obtaind, melting at 110° C. (ethyl acetate).

Analysis for C$_{12}$H$_{15}$NO$_4$S (269.38): Calculated: C 53.50%, H5.61%, N 5.20%; Found: C 53.38%, H 5.77%, N 5.47%.

IR spectrum (KBr): 2950, 1735 cm$^{-1}$.

$^1$-H-NMR spectrum (CDCl$_3$): δ2.86 s (3H); 2.65–3.0 m (2H); 3.75 m (1H); 4.1–4.7 m (4H); 7.25 s (5H).

EXAMPLE 24

Ethyl 1-phenyl-4-oxo-2-azetidine-carboxylate 151 g. (0.52 moles) of diethyl 1-phenyl-4-oxo-2,2-azetidine-dicarboxylate [J. C. Sheehan, A. K. Bose: J. Am. Chem. Soc. 72, 5158 (1950)] in 150 ml. of dimethylsulfoxide, in the presence of 36.5 g. of sodium chloride and 18.7 ml. (1.04 moles) of water are stirred on an oil bath of 170° to 180° C. for 4 to 5 hours. The reaction mixture is poured onto 1350 ml. of water, shaken with three 200-ml. portions of diethyl ether and the phases are separated. The aqeuous phase is saturated with sodium chloride and shaken with three 100-ml. portions of ether. The combined ethereal solution is dried with magnesium sulfate, filtered and the filtrate is evaporated to yield 106.5 g. (94%) of the named compound, melting at 34° to 36° C.

IR spectrum (KBr): 2900, 1750–1720 cm$^{-1}$.

$^1$H-NMR spectrum (CDCl$_3$): δ1.25 t (3H); 3.25 m (2H); 4.25 q (2H); 4.5 m (1H); 7.3 s (5H).

EXAMPLE 25

1-Phenyl-4-(hydroxymethyl)-2-azetidinone

To a dilution of 106.5 g. (0.486 moles) of ethyl 1-phenyl-4-oxo-2-azetidine-carboxylate prepared according to Example 24 in 700 ml. of methanol 18.74 g. (0.493 moles) of sodium tetrahydrido-borate(III) are added with outer cooling with ice water and stirring. The mixture is acidified with dilute hydrochloric acid and it is then neutralized with disodium hydrogenphosphate. Methanol is distilled off in vacuo. 65 g. (76%) of the named compound are obtained, melting at 100° to 102° C. (ethyl acetate/petroleum ether).

Analysis for C$_{10}$H$_{11}$NO$_2$ (177.20): Calculated: C 67.78%, H 6.26%, N 7.91%; Found: C 67.52%, H 6.19%, N 8.20%.

EXAMPLE 26

1-Phenyl-4-(mesyloxymethyl)-2-azetidinone

To a solution of 15 g. (0.085 moles) of 1-phenyl-4-(hydroxymethyl)-2-azetidinone prepared according to Example 25 in 40 ml. of pyridine 7.7 ml. (11.7 g., 0.10 moles) of mesyl chloride are added dropwise, with outer cooling with ice water, with stirring. The mixture is stirred for one hour, whereupon 100 ml. of water are slowly added. The crystalline precipitate is filtered off to yield 18.8 g. (87%) of the named compound, melting at 86° to 87° C. (ethanol).

Analysis for C$_{11}$H$_{13}$NO$_4$S (255.28): Calculated: C 51.75%, H 5.13%, N 5.49%, S 12.56% Found: C 52.18%, H 5.10%, N 5.38%, S 12.41%.

IR Spectrum (KBr): 2950, 1740 cm$^{-1}$.

$^1$H-NMR spectrum (CDCl$_3$): δ2.9 s (3H); 3.1–3.3 m (2H); 6.3–6.6 m (3H); 7.2–7.5 m (5H).

EXAMPLE 27

1-Phenyl-4-(iodomethyl)-2-azetidinone 18.8 g. (0.074 moles) of 1-phenyl-4-(mesyloxymethyl)-2-azetidinone prepared according to Example 26 in 80 ml. of dry acetone are boiled with 18.8 g. (0.125 moles) of sodium iodide for 4 hours, with stirring. 100 ml. of water are added to the reaction mixture, the crystalline precipitate is filtered off and recrystallized from ethanol: 18.1 g. (89%) of the named compound are obtained.

Analysis for $C_{10}H_{10}INO$ (287.10): Calculated: C 41.83%, H 3.51%, N 4.88 %, I 44.20% ; Found: C 41.61%, H 3.85%, N 5.07%, I 44.77%.

IR spectrum (KBr): 1735 cm$^{-1}$.

$^1$H-NMR spectrum (CDCl$_3$): δ2.80 dd (1H); 3.27 dd (1H); 3.35 dd (1H); 3.73 dd (1H); 4.14 m (1H); 7.30 m (5H).

$^{13}$C-NMR (CDCl$_3$): δ6.08; 44.41; 51.15; 116.74; 124.08; 124.24; 129.32; 162.90.

EXAMPLE 28

1-Phenyl-4-(chloromethyl)-2-azetidinone

To a solution of 22.5 g. (0.127 moles) of 1-phenyl-4-(hydroxymethyl)-2-azetidinone in 50 ml. of dry pyridine 15 ml. of mesyl chloride are added dropwise, under boiling. The solution is stirred for half an hour and is then poured onto 400 ml. of water. The crystalline precipitate is filtered off, washed with water and recrystallized from ethanol. 13.2 g. (53%) of the compound named are obtained, melting at 97° to 98° C. (ethanol).

Analysis for $C_{10}H_{10}ClNO$ (195.65):

Calculated: C 61.39%, H 5.15%, Cl 18.12%, N 7.16%; Found: C 61.13%, H 5.26%, Cl 18.17%, N 7.20 %.

EXAMPLE 29

4-(Cyanomethyl)-1-phenyl-2-azetidinone 1. g. (3.5 mmoles) of 1-phenyl-4-(idoomethyl)-2-azetidinone prepared according to Example 27 in 5 ml. of dimethyl formamide are stirred with 0.4 g. (8 mmoles) of sodium cyanide at 0° C. for 24 hours. The reaction mixture is then poured onto 20 ml. of saturated aqueous sodium chloride solution and extracted with three 30-ml. portions of ether. The ethereal solution is dried with magnesium sulfate, filtered and the filtrate is evaporated in vacuo. The obtained yellow oil crystallizes instantaneously to yield 0.6 g. (91%) of the named compound, melting at 97° to 98° C. (2-propanol).

Analysis for $C_{11}H_{10}N_2O$ (186.2): Calculated: C 70.95%, H 5.41%, N 15.04%; Found: C 71.24%, H 5.93%, N 15.34%.

IR spectrum (KBr): 2920, 2270, 1750 cm$^{-1}$.

EXAMPLE 30

Diethyl benzyhydryl-amino-malonate 40 g. (0.218 moles) of benzhydryl amine and 26.2 g. (18.7 ml., 0.109 moles) of diethyl bromomalonate are allowed to stand at room temperature for one week, while the mixture is stirred from time to time. The solidified mixture is triturated with ether, the crystalline substance obtained is filtered off and thus the excess of benzhydryl amine is separated in the form of hydrobromide. The ethereal mother liquor is evaporated, the residual oil is dissolved in 100 ml. of ethanol and allowed to stand in deep freezer. A small amount of a crystalline precipitate is obtained, which is filtered off. The ethanol solution is evaporated. 24.2 g. of the title compound are obtained, which can be used for the further reactions without purification.

EXAMPLE 31

Diethyl N-benzhydrile-N-(chloroacetyl)-amino-malonate 23.8 g. (69.7 mmoles) of diethyl benzhydryl-amino-malonate prepared according to Example 30 and 11.8 g. (8.3 ml., 104.6 mmoles) of chloroacetyl chloride in 120 ml. of dry benzene are boiled for 15 hours. The mixture is shaken with an 5% aqueous sodium hydrogencarbonate solution and then with water. The organic phase is dried with magnesium sulfate, filtered and the filtrate is evaporated. The residue is crystallized by trituration with a mixture of ether and petroleum ether. 12.2 g. (42%) of the title compound are obtained, melting at 98° to 100° C.

IR spectrum (KBr): 3050, 2950, 1740 br. 1680 cm$^{-1}$.

$^1$H-NMR spectrum (CDCl$_3$): δ1.20 t (6H); 4.05 s (2H); 4.06 q (2); 4.38 s (1H); 6.5 s (1H); 7.38 s (5H).

EXAMPLE 32

Diethyl 1-benzhydrile-4-oxo-2,2-azetidinedicarboxylate.

4.2 g. (10 mmoles) of diethyl N-benzhydril-N-(chloroacetyl)-amino-malonate prepared according to Example 31 in 30 ml. of dry benzene are stirred with 1.82 ml. (1.31 g., 13 mmoles) of triethyl amine for one day at room temperature. The mixture is shaken with dilute aqueous hydrochloric acid solution and then with water. The organic phase is dried with magnesium sulfate, filtered and the filtrate is evaporated. The oily residue is triturated with petroleum ether. 3. g. (79%) of the named compound are obtained, melting at 65° C.

$^1$H-NMR spectrum (CDCl$_3$): δ1.11 t (6H); 3.35 s (2H); 3.96 q (4H); 5.68 s (1H); 7.2 s (10 H).

EXAMPLE 33

Ethyl 1-benzhydril-4-oxo-2 -azetidinecarboxylate 2.5 g. (6.6 mmoles) of diethyl 1-benzhydryl-4-oxo-2,2-azetidine-dicarboxylate prepared according to Example 32 in 5 ml. of dimethyl sulfoxide are stirred in the presence of 0.46 g. (7.9 mmoles) of sodium chloride and 0.24 ml. (13.2 mmoles) of water for 6 hours on an oil bath of 180° C. The mixture is poured onto 20 ml. of saturated aqueous sodium chloride solution, shaken with three 20ml. portions of ether, the ethereal solution is dried with magnesium sulfate, filtered and the filtrate is evaporated. 1.8 g. (89%) of the named compound are obtained.

$^1$H-NMR spectrum (CDCl$_3$): δ1.10 t (3H); 3.07 m (2H); 3.73–4.09 m (3H); 5.93 s (1H); 7.26 s (10H).

EXAMPLE 34

1-Benzhydryl-4-(hydroxymethyl)-2-azetidinone

To a solution of 1.3 g. (4.2 mmoles) of ethyl 1-benzhydryl-4-oxo-2-azetidine-carboxylate in 5 ml. of methanol 0.32 g. (8.4 mmoles) of sodium tetrahydridoborate(III) are added with outer cooling with ice water and stirring. The mixture is stirred for 10 minutes, whereupon it is poured onto 20 ml. of water and shaken with three 10-ml. portions of ethyl acetate. The ethyl acetate solution is dried with magnesium sulfate, filtered and the filtrate is evaporated. The oily residue is crystallized by trituration with 10 ml. of ether. 0.82 g. (73%) of the named compound are obtained, melting at 101° to 102° C. (ethyl acetate/petroleum ether).

Analysis for $C_{17}H_{17}NO_2$ (267.32): Calculated: N 5.24%; Found: N 4.96%.

$^1$H-NMR spectrum (CDCl$_3$): δ2.04 sz s (1H); 2.84 m (2H); 3.40 m (2H); 3.70 m (1H); 5.96 s (1H); 7.25 s (10H).

EXAMPLE 35

The reaction steps disclosed in Examples 7(a) and 7(b) can be carried out also in combination, without isolating the product of Example 1(a) as follows:

109.7 g. (0.66 moles) of 2,4-dimethoxybenaldehyde and 72 ml. (0.66 moles) of benzylamine in 660 ml. of methanol are stirred at room temperature for 20 minutes (initially a suspension and then a clear solution is obtained), whereupon small portions of 13.2 g. (0.33 moles) of sodium tetrahydrido-borate(III) are added to the solution under outer cooling with ice water.

The progress of the reaction is monitored by thin layer chromatography (Kieselgel G; according to Stahl, a 9:1 mixture of benzene and acetone). When the reaction is complete, the mixture is evaporated to dryness in vacuo, to the residue 300 ml. of water are added and it is shaken with 500 ml. of ether. The aqueous phase is extracted with two further 200 m-l. portions of ether. The combined ethereal phase is dried with magnesium sulfate, filtered and to the ethereal solution 112 ml. (0.66 moles) of diethyl bromomalonate and 93 ml. (0.66 moles) of triethyl amine are added. The reaction mixture is stirred at room temperature for 2 to 3 days. The precipitated triethyl ammoniumbromide is filtered and washed with ether. The mother liquor is evaporated and the residue is crystallized from 150 ml. of ethanol. Thus 210 g. of a crude product are obtained, which is recrystallized from 400 ml. of ethanol. 197 g. (72%) of diethyl N-benzyl-N-(2,4-dimethoxybenzyl)-aminomalonate are obtained. The physical characteristics of the product are identical with those of the product of Example 1(b).

We claim:

1. A compound of the formula (IV)

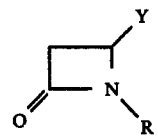

wherein
R is benzyl or benzhydryl;
Y is a group of the formula —COOZ or —CH$_2$M, in which
Z is lower alkyl and
M is hydroxyl, halogen, cyano, or a group of the formula —O—SO$_2$—R$^2$ in which R$^2$ is lower alkyl or tolyl.

2. The compound defined in claim 1 which is ethyl 1-benzyl-4-oxo-2-azetidine-carboxylate.

3. The compound defined in claim 1 which is 1-benzyl-4-(hydroxymethyl)-2-azetidinone.

4. The compound defined in claim 1 which is 1-benzyl-4-(mesyloxymethyl)-2-azetidinone.

5. The compound defined in claim 1 which is ethyl-1-benzyhydryl-4-oxo-2-azetidine-carboxylate.

6. The compound defined in claim 1 which is 1-benzhydryl-4-hydroxymethyl-2-azetidinone.

7. 4-(cyanomethyl)-1-(2,4-dimethoxybenzyl)-2-azetidinone.

* * * * *